United States Patent
Brewer et al.

(10) Patent No.: US 8,205,913 B2
(45) Date of Patent: Jun. 26, 2012

(54) RESPIRATORY TRIPLE SWIVEL MANIFOLD

(75) Inventors: John Brewer, Marietta, GA (US);
Cassandra E. Morris, Roswell, GA (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 728 days.

(21) Appl. No.: 12/347,422

(22) Filed: Dec. 31, 2008

(65) Prior Publication Data
US 2010/0163022 A1    Jul. 1, 2010

(51) Int. Cl.
*F16L 41/00* (2006.01)
(52) U.S. Cl. ............. 285/130.1; 285/131.1; 128/202.27; 128/912
(58) Field of Classification Search ............... 285/133.3, 285/131.1, 132.1, 130.1; 128/202.27, 912
See application file for complete search history.

(56) References Cited

U.S. PATENT DOCUMENTS

| | | | |
|---|---|---|---|
| 1,964,474 A * | 6/1934 | Lindquist | 285/133.3 |
| 3,978,854 A | 9/1976 | Mills, Jr. | |
| 4,240,417 A | 12/1980 | Holever | |
| 4,351,328 A | 9/1982 | Bodai | |
| 4,569,344 A | 2/1986 | Palmer | |
| 5,220,916 A | 6/1993 | Russo | |
| 5,694,922 A | 12/1997 | Palmer | |
| 5,730,123 A * | 3/1998 | Lorenzen et al. | 128/202.27 |
| 5,735,271 A | 4/1998 | Lorenzen et al. | |
| 6,012,451 A * | 1/2000 | Palmer | 128/202.27 |
| 6,415,789 B1 | 7/2002 | Freitas et al. | |
| 6,494,203 B1 * | 12/2002 | Palmer | 128/202.27 |
| 6,612,304 B1 | 9/2003 | Cise et al. | |
| 6,615,835 B1 | 9/2003 | Cise et al. | |
| 6,935,339 B2 | 8/2005 | Mattar Neto et al. | |
| 7,188,623 B2 | 3/2007 | Anderson et al. | |
| 7,263,997 B2 | 9/2007 | Madsen et al. | |
| 7,556,041 B2 * | 7/2009 | Madsen | 128/912 |
| 2008/0210242 A1 | 9/2008 | Burk et al. | |

OTHER PUBLICATIONS (ISO) International Standard 5356, "Anaesthetic and Respiratory Equipment—Conical Connectors. Part 1: Cones and Sockets," Third Edition, 2004, 21 pages.

* cited by examiner

*Primary Examiner* — David E Bochna
(74) *Attorney, Agent, or Firm* — James B. Robinson; Sue C. Watson

(57) ABSTRACT

A respiratory triple swivel manifold is provided which has a base port, which is coupled to a central body. The central body has two laterally-positioned arms, and each arm has a lateral port. Each base port and each lateral port has an inner sleeve which is movable relative to its port. The manifold also has a proximal port coupled to the central body, which may or may not have a rotatable inner sleeve. At least one of the arms and its respective lateral port is positioned at an angle in a range of greater than 90 degrees but less than 180 degrees relative to the central body. Desirably, the base port, the central body and its arms and their respective ports form a Y-shape. The proximal port may intersect the Y-shaped manifold. The base port includes a ramp to direct an object moved through one port into a passageway of the manifold and through the base port to an endotracheal tube without folding, twisting or bunching of any portion of the object within the manifold.

14 Claims, 4 Drawing Sheets

RESPIRATORY TRIPLE SWIVEL MANIFOLD

BACKGROUND

The inventions disclosed herein relate generally to improved medical care for intubated patients, and more particularly to a novel multiple access respiratory manifold for ventilating, aspirating, monitoring, sampling, and providing therapeutic delivery to the respiratory tracts of intubated patients, including infants, adolescents, and adults.

Respiratory patient care is a dynamically developing field in medicine, ranging in its needs from infants to the aged. The range of respiratory ailments, both temporary and permanent, to which such patients are subjected, are many and varied. For example, the range of procedures for intubated patients may include the following: ventilation, aspiration, oxygenation, sampling, visual inspection, in-line sensing, pressure monitoring, flushing, medicating and/or lavage. Most problems now center or focus on multiple needs of the patient and accommodation of multiple treatments, some to be performed at the same time. The lack of equipment to facilely, efficiently, and safely accomplish the multiple therapies in the best interest of the patient has been and continues to be a concern.

When patients receive multiple respiratory therapies or treatments while intubated, problems may occur, including problems with a respiratory access manifold. Multiple devices may need to be coupled to a respiratory manifold. These multiple devices may pull, twist, torque, or otherwise put undesirable pressure on the respiratory manifold. This unwanted pressure or torque may then be passed on to the endotracheal tube, and even a patient's throat or upper respiratory tract. There is a need, however, to provide a common manifold through which all necessary devices are coupled, in order to reduce infection.

Such a respiratory access manifold desirably has multiple ports, and a majority of the ports desirably have some degree of movability to reduce pressure, tension and/or torque on the endotracheal tube. Such a manifold desirably permits quickly and easily coupling and removal of a variety of devices without compromising the quality of health care to the patient. Such a device desirably operates well within a closed circuit ventilating system.

SUMMARY OF THE INVENTION

In response to the difficulties and problems discussed herein, a respiratory triple swivel manifold is provided. The manifold includes a base port. The base port has an inner sleeve which is rotatable relative to the base port. The base port also has a central body. Two arms are coupled to the central body. Each arm has a lateral port. Each lateral port has an inner sleeve which is rotatable relative to the lateral port. The manifold also has a proximal port coupled to the central body. The base port, the central body, each arm and its lateral port and the proximal port cooperate to provide a passageway to an endotracheal tube. At least one arm and its lateral port is positioned at an angle in a range of greater than 90 degrees but less than 180 degrees relative to the central body. The base port includes a ramp to direct an object moved through one other port into the passageway and through the base port to an endotracheal tube coupled to the base port without any portion of the object folding, twisting or bunching within the manifold.

In another aspect of the invention, a respiratory triple swivel manifold is provided. The manifold comprises a base port. The base port includes an inner sleeve which is movable relative to the base port. The manifold also includes a central body coupled to the base port. The central body has two arms. Each arm has a lateral port, and each lateral port has an inner sleeve which is movable relative to the lateral port. The base port, the central body, and the arms and their lateral ports cooperate to form a Y-shape. The manifold also includes a proximal port, which is coupled to the central body. The proximal port intersects the Y-shape created by the combination of the base port, the central body and the arms and their lateral ports. The base port, the central body, each lateral port and the proximal port cooperate to provide a passageway to an endotracheal tube. The base port includes a ramp to direct an object moved through one other port into the passageway and through the base port to an endotracheal tube without any portion of the object folding, twisting or bunching within the manifold.

DEFINITIONS

As used herein the following terms have the specified meanings, unless the context demands a different meaning, or a different meaning is expressed; also, the singular generally includes the plural, and the plural generally includes the singular unless otherwise indicated.

As used herein, the terms "comprise," "comprises," "comprising" and other derivatives from the root term "comprise" are intended to be open-ended terms that specify the presence of any stated features, elements, integers, steps, or components, but do not preclude the presence or addition of one or more other features, elements, integers, steps, components, or groups thereof. Similarly, the terms "include", "includes", "including," as well as the terms "has", "have", "having" and derivatives thereof, are intended to be interpreted as the word "comprise", and are intended to be open-ended terms that specify the presence of any stated features, elements, integers, steps, or components, but do not preclude the presence or addition of one or more other features, elements, integers, steps, components, or groups thereof.

As used herein, the term "port" means a structure providing an opening into or through a component for the passage of an object and/or a liquid and/or a gas.

As used herein, the term "torque" means a force that produces or tends to produce rotation or torsion.

As used herein, the phrase "operable communication" means a transmission or passage for a between two points and/or two structures for a specific purpose. In this example, operable communication would be a passage which permits gasses to pass, and may also be configured to permit objects to pass.

As used herein the term "suction catheter" means long, flexible tubes used to remove secretions from the airway and are available in many sizes, commonly from 10 to 20 French and varying lengths, typically from 15 to 25 inches (38 to 64 cm). Suction catheters may be made from latex and other polymers.

Suction catheters are well known and widely commercially available for many medical uses. Suctioning may be performed using an "open" or "closed" system. In the open system, the suction catheter is merely a flexible plastic tube that is inserted into the flexible lumen with a source of suction connected to the proximal end of the suction catheter. Anything that the suction catheter touches before entering the lumen must be maintained in a sterile condition so a "sterile field" must be created on or next to the patient. The suction catheter must be carefully handled after it is used since it will be coated with the patient's secretions. In contrast, in the "closed" system, for example that disclosed in commonly owned U.S. Pat. No. 4,569,344, a device which may be used to suction secretions is enclosed within a generally cylindrical plastic bag to eliminate or minimize contamination of the suction catheter prior to use. This is generally referred to as a "closed suction catheter" and is available under the tradename TRACH CARE® from BALLARD® Medical Products (Kimberly-Clark Corporation). As the patient requires artificial removal of secretions, the suction catheter may be advanced through one end of the plastic bag, through a connecting fitting and into the flexible lumen. The other, proximal end of the suction catheter is attached to a source of suction. Suction may be applied using, for example, a finger controlled valve on the proximal end of the suction catheter, and the secretions removed. Secretions are thus drawn into the lumen of the suction catheter tube and removed and the system remains closed. The suction catheter is subsequently withdrawn from the flexile lumen and back into the plastic bag to keep the circuit closed. Closed suction systems are generally preferred by healthcare providers since the provider is better protected from the patient's secretions. Closed suction systems are also easier and quicker to use since a sterile field need not be created each time the patient must be suctioned, as is required in open suction systems. The closed suction catheter may be permanently attached to the proximal end of the flexible lumen or may be detachably connected so that it may be replaced periodically.

As used herein, the terms "pathway" and/or "passageway" includes the components defined herein which are or may be coupled to an object or a device, such as, for example only, a suction catheter assembly which provide an opening to permit an object or a device, such as a suction catheter, to be moved therethrough to an endotracheal tube.

As used herein, the term "couple" includes, but is not limited to, joining, connecting, fastening, linking, tying, adhering (via an adhesive), or associating two things integrally or interstitially together.

As used herein, the term "configure" or "configuration", and derivatives thereof means to design, arrange, set up, or shape with a view to specific applications or uses. For example: a military vehicle that was configured for rough terrain; configured the computer by setting the system's parameters.

As used herein, the terms "substantial" or "substantially" refer to something which is done to a great extent or degree; a significant or great amount; for example, as used herein "substantially" as applied to "substantially" covered means that a thing is at least 70% covered.

As used herein, the term "alignment" refers to the spatial property possessed by an arrangement or position of things in a straight line.

As used herein, the terms "orientation" or "position" used interchangeably herein refer to the spatial property of a place where or way in which something is situated; for example, "the position of the hands on the clock."

As used herein, the term "about" adjacent to a stated number refers to an amount that is plus or minus ten (10) percent of the stated number.

These terms may be defined with additional language in the remaining portions of the specification.

DETAILED DESCRIPTION OF THE INVENTION

Figure 1:
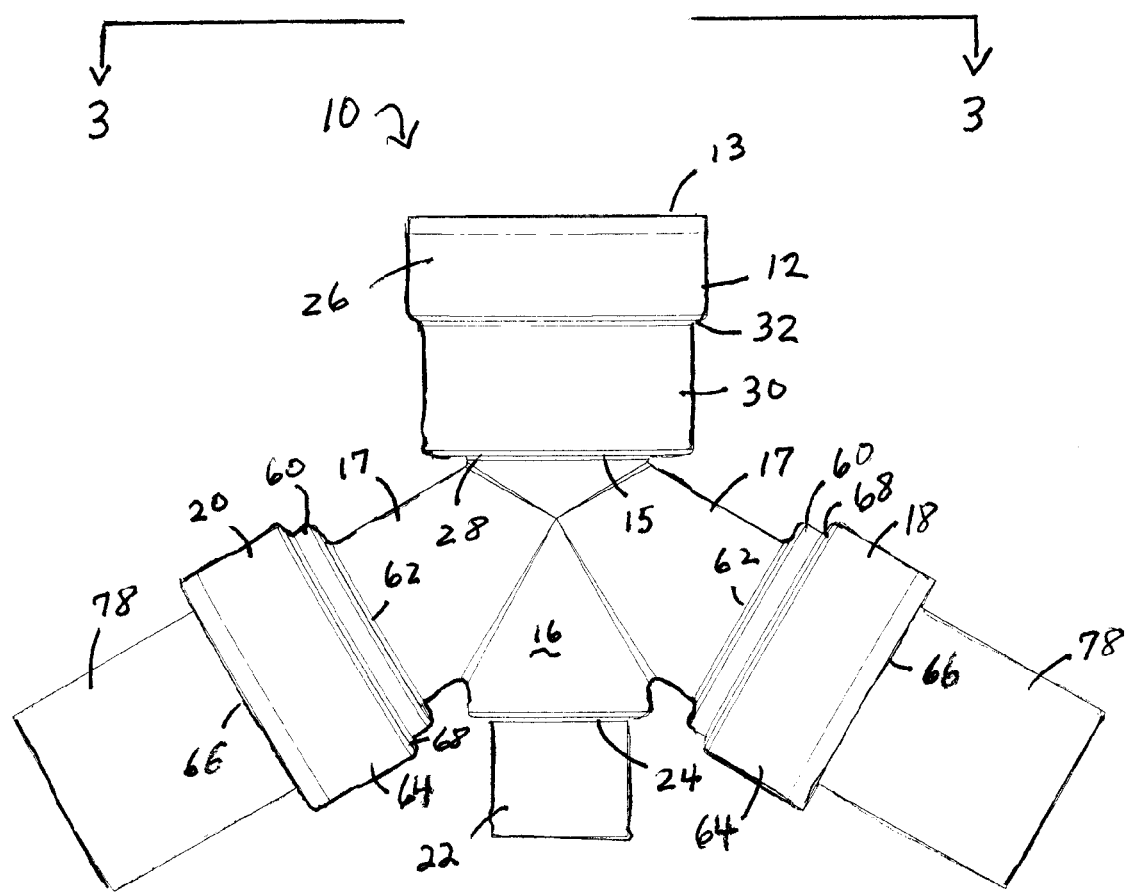
FIG. 1 is a plan view of the respiratory triple swivel manifold of the present invention.

Reference will now be made in detail to one or more embodiments of the invention, examples of the invention, examples of which are illustrated in the drawings. Each example and embodiment is provided by way of explanation of the invention, and is not meant as a limitation of the invention. For example, features illustrated or described as part of one embodiment may be used with another embodiment to yield still a further embodiment. It is intended that the invention include these and other modifications and variations as coming within the scope and spirit of the invention.

Current designs for manifolds which couple to an endotracheal tube, a ventilator, and a suction catheter assembly only provide three openings or ports. If another device needs to be added, then one device must be removed, and the closed ventilating system may need to be opened to permit its addition. Opening a closed ventilating system can lead to infection, as noted previously. The present invention describes a triple swivel manifold which permits multiple access for additional objects, devices or instruments, and reduces or removes the need to open a closed ventilating system.

Figure 2:
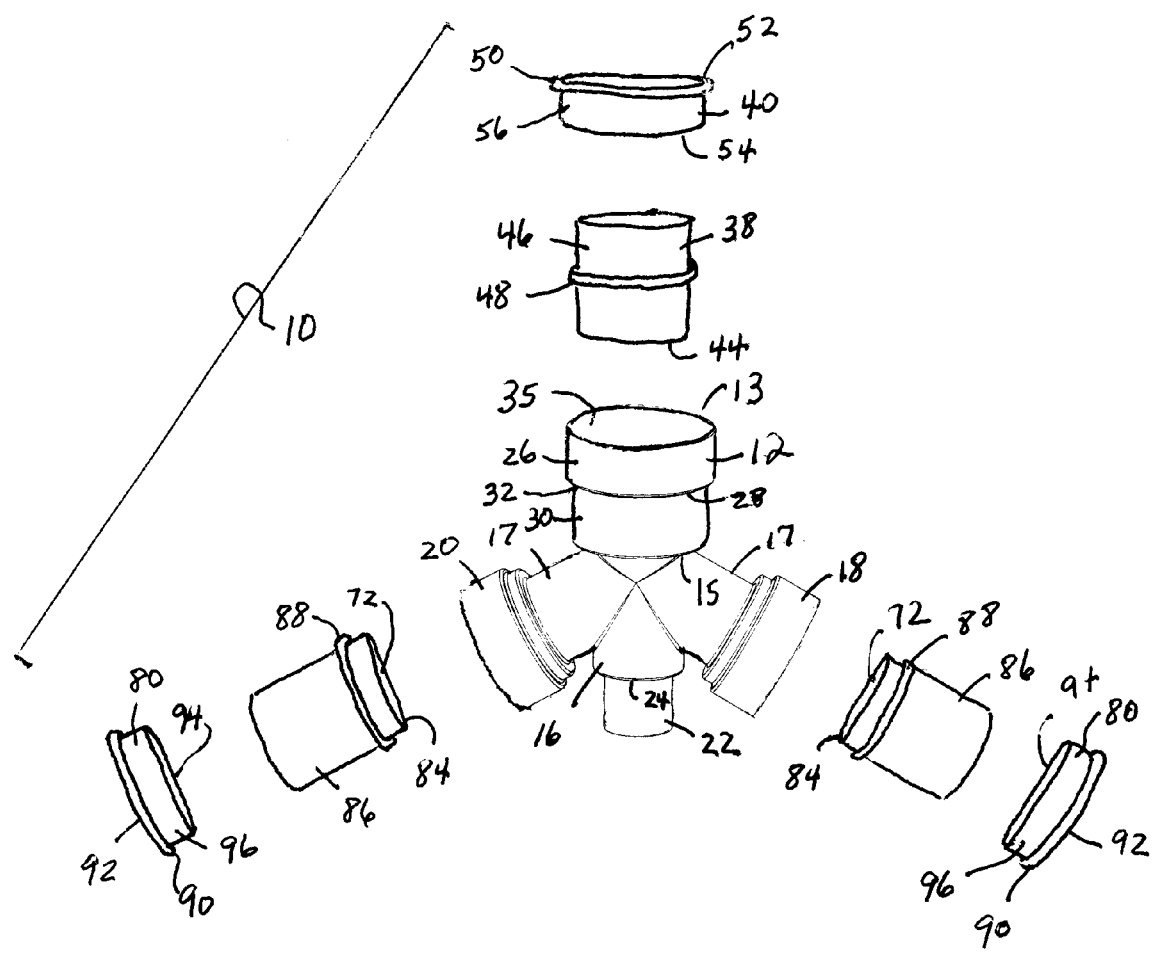
FIG. 2 is an exploded view of the embodiment of FIG. 1.
Figure 3:
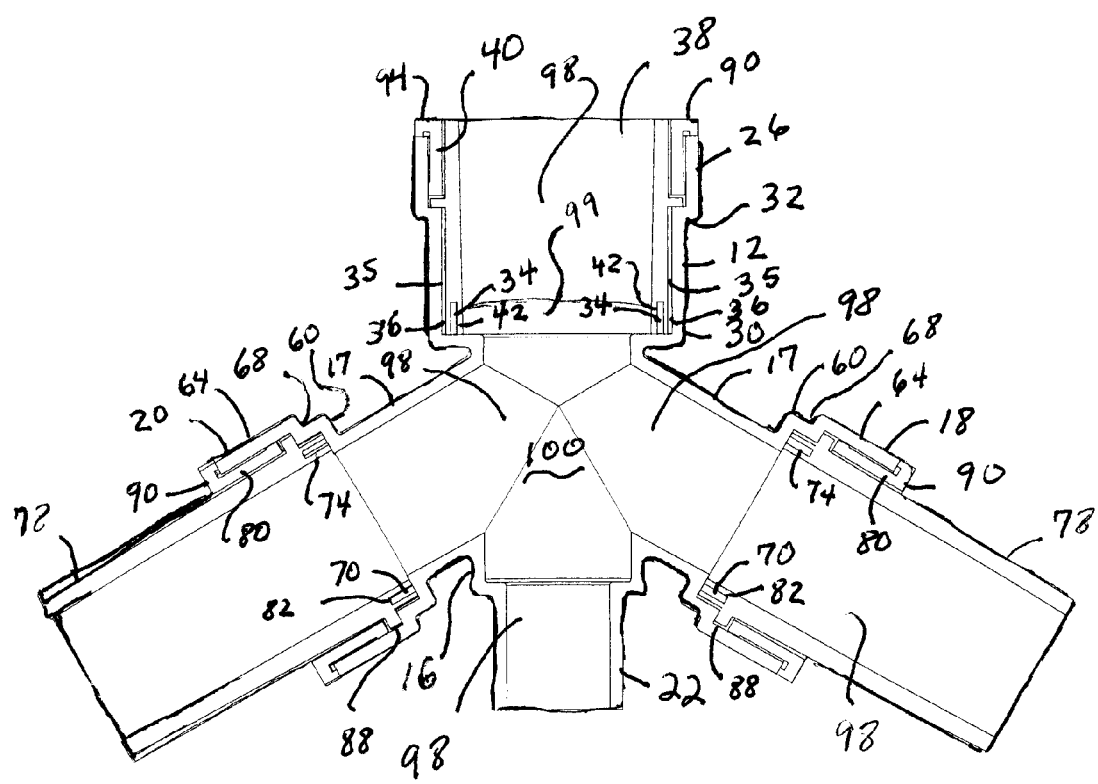
FIG. 3 is a cross-sectional view of FIG. 1 taken along lines 3-3.
Figure 4:
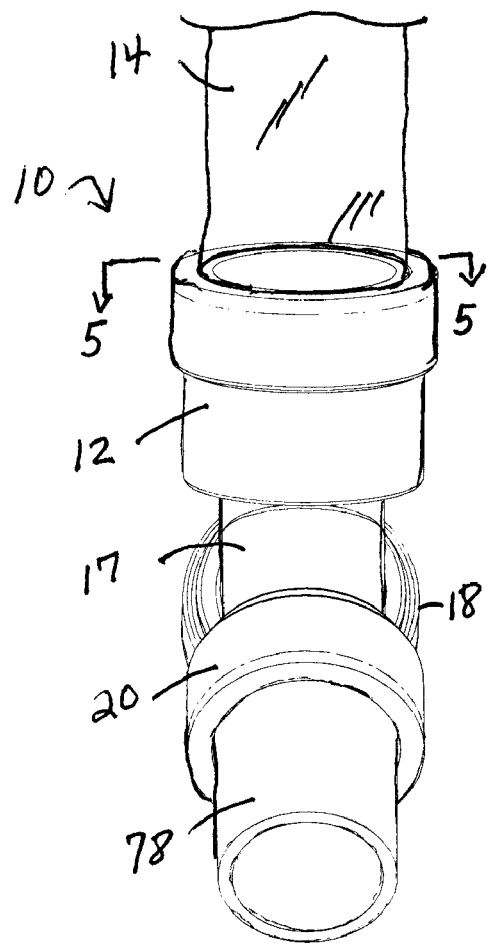
FIG. 4 is a side view of the embodiment of FIG. 1.

Turning now to the drawings, as illustrated in FIGS. 1-5, a respiratory triple swivel manifold 10 is provided. The manifold 10, as shown in FIGS. 1 and 2, includes a hollow, cylindrically-shaped distal base port 12 which desirably, but not by way of limitation, couples at its distal end 13 to a proximal end of an endotracheal tube 14 (FIG. 4). The base port 12 includes a generally hollow cylindrically-shaped central body 16 which is desirably axially aligned with the base port 12 and which is provided on a proximal end 15 of the base port 12. The central body 16 is formed to include a pair of opposing hollow cylindrically-shaped arms 17, each having a lateral port 18, 20 provided thereon. A generally hollow cylindrically-shaped proximal port 22 is formed on a proximal end 24 of the central body 16. It will be understood that the ports 12, 18, 20 and 22 and central body 16 cooperate to provide an opening threrethrough. While the ports 12, 18, 20 and 22 and body 16 are generally provided on the same plane, it will be appreciated that this is not intended as a limitation, and the four ports 12, 18, 20 and 22 and/or body 16 may each, or in combination, be formed on separate planes and/or axes. Further, while the configuration(s) herein will often be described as "generally cylindrical", it will be understood that this description is not intended as a limitation, and that any configuration or combination of configurations which operate as shown and/or described herein may be utilized.

Turning to FIGS. 2 and 3, the base port 12 includes a distal stepped portion 26 which is provided at a distal end 28 of the base port 12 and a proximal stepped portion 30 which is provided near the proximal end 15 of the base port 12. The distal stepped portion 26 has a larger diameter relative to the proximal stepped portion 30, and the portions 26, 30 are separated by a ledge 32 which provides the transition between the portions 26, 30. The proximal stepped portion 30 includes a lip 34 at the proximal end 15 which extends toward the distal end 28, and the space between an inner surface 35 of the base port 12 and the lip 34 provides a generally U-shaped groove 36.

The base port 12 also includes a long sleeve 38 and a short sleeve 40. The long sleeve 38 and short sleeve 40 desirably are configured to be positioned adjacent an inner surface 35 of the base port 12. The long sleeve 38 includes a groove 42 formed at a proximal end 44 thereof which is configured to receive the lip 34 of the proximal stepped portion 30 therein. An outer surface 46 of the long sleeve 38 has a collar 48 formed thereabout. The short sleeve 40 has an inner diameter which is slightly larger than an outer diameter of the long sleeve 38. The short sleeve 40 also has a collar 50 formed at a distal end 52 thereof.

The proximal end 44 of each long sleeve 38 is desirably positioned in the base port 12 so that, as previously described, the lip 34 of the proximal stepped portion 30 of the base port 12 is held within the groove 42 of the long sleeve 38. The collar 48 on each long sleeve 38 desirably contacts the ledge 32 of the base port 12. Each short sleeve 40 is desirably positioned so that a proximal end 54 is positioned against the collar 48 of the long sleeve 38 so that its cylindrical body 56 is positioned between the outer surface 46 of the long sleeve 38 and the inner surface 35 of the base port 12, to allow rotation of the long sleeve 38 but to prevent the long sleeve 38 from moving out of the base port 12, although this is not intended as a limitation. In fact, some movement of the long sleeve 38 axially within the base port 12 may be desirably at times (not shown). The collar 50 on the short sleeve 40 of the base port 12 extends radially outward against the distal end 13 of the base port 12, and desirably seals against it. Desirably, an adhesive or other sealing means (for example, but not by way of limitation, O-rings, silicone, and the like) may be used to seal the short sleeve 40 to the base port 12, thereby permitting the long sleeve 38 to move or rotate within the base port 12. A seal (not shown) may also be applied to the proximal end 44 of the long sleeve 38, however, such a seal desirably permits the long sleeve 38 to rotate and move relative to the base port 12. Such movement may be rotational and axial as well.

The lateral ports 18, 20 of each arm 17 each include a distal stepped portion 60 which is provided near a distal end 62 of each lateral port 18, 20 and a proximal stepped portion 64. The distal stepped portion 60 has a smaller diameter relative to the proximal stepped portion 64, and the portions 60, 64 are separated by a ledge 68 which provides the transition between the portions 60, 64. The distal stepped portion 60 desirably includes a lip 70 provided at the distal end 62 of each lateral port 18, 20 which extends toward the proximal end 66 of each port 18, 20. The space between an inner surface 72 of each lateral port 18, 20 and the lip 70 may provide a generally U-shaped groove 74.

Each lateral port 18, 20 also includes a long sleeve 78 and a short sleeve 80. The long sleeve 78 and short sleeve 80 desirably are configured to be positioned adjacent the inner surface 72 of each lateral port 18, 20. The long sleeve 78 includes a groove 82 formed at a distal end 84 thereof which configured to receive the lip 70 of the distal stepped portion 60 therein. An outer surface 86 of the long sleeve 78 has a collar 88 formed thereabout, near its distal end 84. The short sleeve 80 has an inner diameter which is slightly larger than an outer diameter of the long sleeve 78. The short sleeve 80 also has a collar 90 formed at a proximal end 92 thereof.

The distal end 84 of each long sleeve 78 is desirably positioned in each lateral port 18, 20 so that, as previously described, the lip 70 of the distal stepped portion 60 of each lateral ports 18, 20 is held within the groove 82 of each long sleeve 78. The collar 88 on each long sleeve 78 desirably contacts the ledge 68 of each lateral port 18, 20.

Each short sleeve 80 is desirably positioned so that a distal end 94 is positioned against the collar 88 of the long sleeve 38 so that its cylindrical body 96 is positioned between the outer surface 86 of the long sleeve 38 and the inner surface 72 of each lateral base 18, 20. In addition, the position of the distal end 94 against the collar 88 permits movement or rotation of each long sleeve 78 within the lateral ports 18, 20. The collar 90 on the short sleeve 80 of each lateral port 18, 20 extends radially outwardly over at least a portion of each proximal end 66 of each lateral port 18, 20 and assists in holding each long sleeve 78 within each lateral port 18, 20. However, it will be appreciated that axial movement of the long sleeve 78 within each lateral port 18, 20 (and any other port shown and/or described herein) is specifically contemplated as well (not shown). The collar 90 of the short sleeve 80 extends over a portion of the proximal end 66 of each lateral port 18, 20 and is desirably sealed thereagainst. Sealing means, such as, but not by way of limitation, adhesives, O-rings, silicone, and the like may be used to seal each short sleeve 80 to each lateral port 18, 20, thereby permitting each long sleeve 78 which extends therefrom to move or rotate within each lateral port 18, 20. A seal (not shown) may also be applied to the distal end 62 of the long sleeve 78, however, such a seal desirably permits the long sleeve 78 to rotate and move relative to the base port 12. Such movement may be rotational and axial as well.

The proximal port 22 extends a distance from the central body 16. The proximal port 22 in the present embodiment is configured as a generally hollow cylinder, is axially aligned with the base port 12 and the central body 16, and it does not include a long or short sleeve therein. However, it will be appreciated that the proximal port 22 may be formed with or without sleeves, and at any angle relative to the central body 16 and/or base port 12, so long as the proximal port operates as shown and/or described herein.

The base port 12 and the lateral ports 18, 20 each permit a device coupled thereto to rotate freely. This rotation greatly reduces the pressure and/or torque produced by devices coupled to these ports (not shown). Moreover, such devices are not likely to become or remain twisted, due to the rotation allowed by the ports. This reduction in pressure and/or torque results in reduced pressure and/or torque exerted on the endotracheal tube 14 (FIG. 4), which results in less pressure and/or torque exerted in the patient's throat. In addition, it permits a health care provider more freedom to maneuver various devices, since such devices will not likely become, or remain, twisted when coupled to the ports 12, 18, 20 of the manifold 10.

The manifold 10 desirably positions the lateral ports 18, 20 away from the base port 12, and at least one of the lateral ports 18, 20 desirably is provided at an angle of greater than 90 degrees but less than about 180 degrees. The other of the lateral ports 18, 20, may be provided at an angle of between about 25 degrees and about 90 degrees.

Therefore, the current configuration of a Y-shape relative to the ports 12, 18, and 20, as illustrated best in FIGS. 1 and 3, is not intended as a limitation, but merely as an example. The ports 12, 18, 20 and 22 of the manifold 10, as illustrated in the present embodiment, reside within the same plane. However, it will be understood that one or more ports may be positioned another plane or axis.

Figure 5:
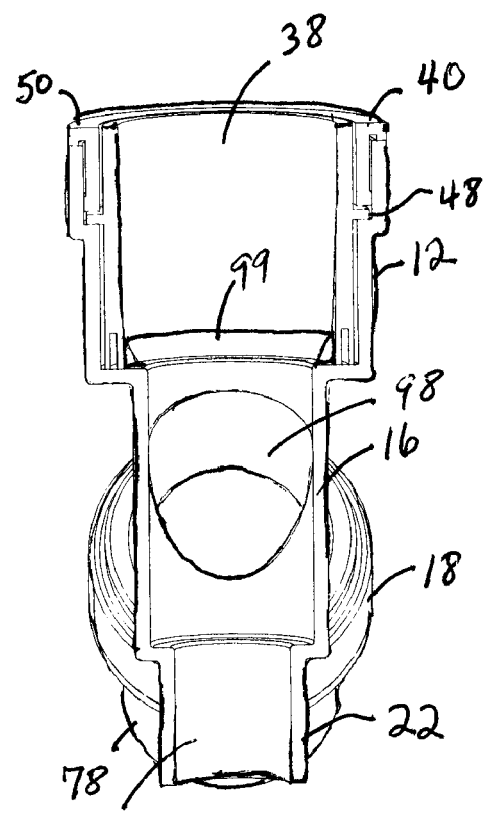
FIG. 5 is a sectional view of FIG. 4 taken along lines 5-5.

The manifold 10 provides an inner surface 98, as shown in FIGS. 3 and 5, in which the junctions of the various arms 17 and ports 12, 22 are coupled to the central body 16. The present intersected Y formation (the proximal port 22 intersects the arms 17 providing the branches of the "Y") assists a health care provider in passing an object or device, such as a suction catheter (not shown) into and through the manifold 10. Such devices are frequently formed from very soft materials, and easily buckle, fold, and bunch if they encounter any irregularity, protuberance, protrusion, or obstruction within the inner surface 98 of the manifold The intersected or forked Y-shape therefore assists in moving an object or device toward the endotracheal tube 14, as illustrated in FIGS. 4 and 5, and a patient's respiratory tract. To assist in this direction, the base port 12 has a ramp 99 which guides a device or object into the base port 12 and therefore into the endotracheal tube 14. The sleeves 38, 40 of the base port 12 and the sleeves 78,80 of the lateral ports 18, 29 provide a smooth, continuous surface without irregularities, protuberances, or protrusions (such as ridges, bumps, edges, collars, and so forth). This design of the manifold 10 creates a passageway or pathway 100 so that such an object or device, such as, for example, but not by way of limitation, a suction catheter, introduced in one port (i.e., 18, 20 or 22) moved steadily through the passageway and through the base port 12 without encountering irregularities which could result in the device buckling, bunching, overlapping itself, and so forth, which would prevent the device from reaching the endotracheal tube and/or a patient's respiratory tract.

The manifold 10 is desirably formed from a polymer. More desirably, the manifold 10 is formed from a polycarbonate, an acrylic, and so forth.

While a central body 16 and arms 17 are utilized in the present embodiment of the manifold 10, it will be appreciated that the base manifold may be formed to provide the cylindrical body 16 (not shown). The lateral ports 18, 20 may formed the arms 17. The proximal port 22 may form a portion of the base port 12 as well (not shown). Alternatively, the arms provide a portion of the lateral ports 18, 20 (not shown). Additional arms and/or ports may also be provided (not shown). It will be appreciated that other alternatives are also possible.

Moreover, it will be understood that one or more sleeves may be formed to extend or move axially within each port as well as rotate (not shown). It will be further understood that one or more sleeves may be releasably locked in a fixed position relative to axial and/or rotational movement (not shown).

While the present invention has been described in connection with certain preferred embodiments it is to be understood that the subject matter encompassed by way of the present invention is not to be limited to those specific embodiments. On the contrary, it is intended for the subject matter of the invention to include all alternatives, modifications and equivalents as can be included within the spirit and scope of the following claims.

What is claimed is:

1. A respiratory triple swivel manifold, comprising:
   a base port, wherein the base port includes an inner sleeve which is rotatable relative to the base port;
   a central body coupled to the base port having two arms, each arm having a lateral port, and each lateral port having an inner sleeve which is rotatable relative to the lateral port; and
   a proximal port coupled to the central body,
   wherein the base port, the central body, each lateral port and the proximal port cooperate to provide a passageway, wherein at least one arm and its lateral port is positioned at an angle in a range of greater than 90 degrees but less than 180 degrees relative to the central body, and
   wherein the base port includes a triangular ramp to direct an object moved through at least one port into the passageway and through the base port to an endotracheal tube coupled thereto, without folding, twisting or bunching of any portion of the object within the manifold.

2. The respiratory triple swivel manifold of claim 1, wherein at least one other arm and its lateral port is positioned at an angle in a range of between about 25 degrees to about 85 degrees.

3. The respiratory triple swivel manifold of claim 1, wherein at least one other arm and its lateral port is positioned at an angle of about 90 degrees.

4. The respiratory triple swivel manifold of claim 1, wherein at least one other arm is positioned at an angle in a range of greater than 90 degrees but less than 180 degrees.

5. The respiratory triple swivel manifold of claim 1, wherein the base port and each lateral port further comprises a short sleeve.

6. The respiratory triple swivel manifold of claim 5, wherein the short sleeve holds a long sleeve in a movable position relative to its port.

7. The respiratory triple swivel manifold of claim 6, wherein the short sleeve holds the long sleeve in a rotatable position relative to its port.

8. The respiratory triple swivel manifold of claim 1, wherein each port includes a lip and a groove formed between the lip and the inner surface of the port.

9. The respiratory triple swivel manifold of claim 8, wherein the base port and each lateral port comprise a short sleeve and a long sleeve, wherein each long sleeve includes a groove formed in one end which is configured to fit within the lip and groove of its respective port.

10. The respiratory triple swivel manifold of claim 1, wherein each port has an inner surface having a larger diameter and a smaller diameter.

11. The respiratory triple swivel manifold of claim 10, wherein the larger diameter and the smaller diameter are connected to an edge which provides a transition between two diameters.

12. The respiratory triple swivel manifold of claim 11, wherein the base port and each lateral port comprise a short sleeve and a long sleeve, wherein each long sleeve includes a collar, and wherein the color contacts the edge.

13. The respiratory triple swivel manifold of claim 12, wherein each short sleeve includes a collar, and wherein each short sleeve contacts an end of the port.

14. The respiratory triple swivel manifold of claim 1, wherein the base port, the central body, and the arms and their lateral ports cooperate to form a Y-shape.

* * * * *